United States Patent [19]

Li et al.

[11] Patent Number: 5,288,763
[45] Date of Patent: Feb. 22, 1994

[54] POROUS, POLYMER BEADS AND PROCESS OF THEIR PREPARATION

[75] Inventors: Nai-Hong Li, Edmonton, Canada; Kam W. Leong, Ellicott City, Md.

[73] Assignee: The Johns Hopkins University School of Medicine, Baltimore, Md.

[21] Appl. No.: 995,793

[22] Filed: Dec. 23, 1992

[51] Int. Cl.⁵ ............................................. C08J 9/26
[52] U.S. Cl. .............................. 521/61; 521/59; 521/60; 521/134; 521/140; 521/149; 521/150
[58] Field of Search .................. 521/60, 61, 149, 150, 521/134, 140, 59

[56] References Cited

U.S. PATENT DOCUMENTS 5,047,438  9/1991  Feibush et al. ..................... 521/61

*Primary Examiner*—Morton Foelak
*Attorney, Agent, or Firm*—Kazuyuki Yamasaki

[57] ABSTRACT

Porous, polymer particles comprising a functionalized cross-linked copolymer having microporous regions and macroporous regions in the polymer matrix thereof, wherein the functional groups are essentially present only within the macroporous regions, as well as processes for preparing these particles based on a template polymerization technique followed by removal of the template polymer from the particles are disclosed. The particles of the invention are useful in chromatography, and in various analytical, diagnostic techniques and solid state peptide, DNA synthesis.

18 Claims, 6 Drawing Sheets

POROUS, POLYMER BEADS AND PROCESS OF THEIR PREPARATION

BACKGROUND OF THE INVENTION

1. Field of the Invention

This invention relates to porous, polymer particles useful in chromatography and in various analytical, diagnostic techniques and solid state peptide, DNA synthesis, as well as to processes for preparing the same by use of a template polymerization technique.

2. Description of Related Art

Small, uniformly-sized, cross-linked, porous polymer beads find use as a low-cost, stable adsorbent in separating and purifying organic and inorganic materials including polymers and biomolecules. Such beads will also find use in chromatographic separation, filtration, gel permeation, and affinity chromatography. Further use can be contemplated as microcarriers for cell culture in addition to as supports for solid-phase peptide or DNA synthesis. These beads should be chemically compatible to organic solvents over a wide range of pH and should have a desired shape, size, porosity and surface area.

Macroporous bead polymers of cross-linked copolymers which contain functionality are, for example, are described in J. R. Benson and D. J. Woo, *J. Chromatographic Sci.*, 1984, 22, 386. They are prepared by conventional suspension polymerization. First, a monomeric material and cross-linkers are suspended as droplets in an emulsion (water/a water-immiscible organic solvent) with the aid of a surfactant. With the addition of an initiator, polymerization proceeds in the droplets to form gel beads containing the solvent entrapped within the polymeric matrix. The solvent entrapped is removed by extraction with a second solvent such as benzene, toluene, chloroform, etc., leaving macropores in the polymer matrix. On the other hand, the cross-linked polymer phase forms micropores in the matrix. Desired functionality is provided on the surface of the polymers by dervatization thereof. However, when the polymer is derivatized, functional groups are introduced to the polymer surfaces within micropores as well as within macropores. Because of the porous nature of the polymer matrix, the derivatization reaction takes place indiscriminately within any pore structure. Since the functional groups in the microporous region can interact with analytes, chromatographic separation using the polymer beads prepared by the method described above is undesirably influenced by such micropore derivatization. This normally leads to ill-defined peak shapes such as tailing due to different fluid dynamics in the microporous and macroporous regions. When the beads are used as a solid support in a DNA synthesizer, the chain growth of oligonucleotides can occur in the macroporous region as well as in the microporous region. After several steps of chain elongation, the resultant oligonucleotides would be contaminated by unwanted oligomers.

U.S. Pat. No. 5,047,438 to Feibush and Li describes a method of preparing porous polymer particles by polymerizing monomers and cross-linkers in the pores of inorganic template particles and by removing the inorganic template particles without destruction of the polymer structure. In this process, the surface of the polymer structure can further be modified in various ways to impart desired functionality. One such technique involves bonding a monomer carrying desired functionality to the copolymer surface during polymerization, followed by removal of the template material. However, all the techniques disclosed in U.S. Pat. No. 5,047,438 allow the copolymer surface to be modified uniformly. Therefore, the resulting modified (functionalized) polymer particles would, for example, not be suitable for high-resolution chromatography.

Accordingly, a new porous polymer bead which overcome the above problems associated with the prior art polymer particles is definitely needed. This invention addresses such need by providing uniform, macroporous, functionalized polymer particles prepared by a template polymerization technique entirely different from the techniques taught in the prior art.

SUMMARY OF THE INVENTION

It has been discovered that porous polymer particles having desired functionality only in their macroporous region, but not in their microporous region can be prepared by a template polymerization technique in which monomers, cross-linkers, and functional monomers having desired functionality are copolymerized in the presence of a template polymer capable of interacting with the desired functionality and, after polymerization, the template polymer is removed with the result that the desired functional groups are only left in the macroporous region of the polymer matrix.

In one aspect of the invention, there is provided porous, functionalized polymer particles comprising a cross-linked copolymer having microporous regions and macroporous regions in the polymer matrix thereof, wherein the functional groups are essentially present only within the macroporous regions.

In another aspect of the invention, there is provided a method of preparing porous, functionalized polymer particles which comprises the steps of:

(a) providing a polymerizable mixture containing a functional monomer, a cross-linker, and a template polymer, in an aqueous medium to obtain a suspension, the template polymer being capable of forming an ionic or covalent bond with the functional monomer;

(b) copolymerizing the monomer and the cross-linker with or without a polymerization catalyst in the suspension to form a cross-linked copolymer;

(c) removing the aqueous medium and the template polymer from the copolymer to recover porous, functionalized polymer particles, the particles having macroporous regions and microporous regions in the polymer matrix thereof, wherein the functional groups are essentially present only within the macroporous regions.

These features, as well as the nature, scope and utilization of this invention will become readily apparent to one skilled in the art from the following description, the drawings, and the appended claims.

DETAILED DESCRIPTION OF THE INVENTION

The present invention is applicable to any copolymers based on monomers carrying desired functionality, additional monomers, and cross-linkers and prepared from the foregoing copolymerizable mixture in the presence of a template polymer in aqueous medium Suitable monomers carrying desired functionality (herein referred to as "functional monomer") include, but not limited to, monoethylenically unsaturated monomers. Representative of the monomers are vinyl monomers such as vinylpyridine (4-vinylpyridine), vinylphenol (4-vinylphenol), and vinyl-p-toluene-sulfonic acid (4-vinyl-p-toluenesulfonic acid), acrylic acid monomers such as acrylic acid and methacrylic acid, including methacrylic acid halide.

Suitable template polymers include, but not limited to, poly(acrylic acid), poly(vinyl alcohol), and poly(4-vinylpyridine), including poly(4-vinylpyridine-co-styrene).

With proper choice of functional monomers and template polymers, association between both molecules can be accomplished either through an ionic or covalent bonding. For example, when vinylpyridine is employed as the functional monomer, it is preferred to use poly(acrylic acid) as the template polymer. Carboxylic acid moieties in the template polymer ionically interact with pyridiyl groups of the monomer such that monomer molecules align along the backbone structure of the template polymer, as shown in the following scheme:

In the case of monomers with acidic functionalities such as carboxylic acid or sulfonic acid, template polymers carrying basic moieties such as pyridyl can preferably be used. Particularly preferred template polymer is poly(4-vinylpyridine).

Another form of template association is a covalent bonding between the template molecule and the monomers, where functional groups present in the monomer molecule react with reactive groups of the template polymer to form covalent bonds. Representative of such covalent bonds are ester and amide. Thus, where a carboxyl group is desired functionality, acrylic acid halide (or methacrylic acid halide) may be used as the functional monomer. The monomer can be linked to a template polymer having hydroxyl such as polyvinyl alcohol by ester formation, as shown in the following scheme:

Suitable cross-linkers include, but not limited to, divinylbenzene, divinyltoluenes, divinylxylenes, divinylnaphthalenes, divinylethylbenzene, ethylene glycol dimethacrylate, glycidyl methacrylate, pentaerythritol trimethacrylate and the polyvinyl ethers of glycol, glycerol, pentaerythritol and resorcinol. Particularly preferred cross-linkers are polyvinylaromatic hydrocarbons such as divinylbenzene. The cross-linkers are necessary in the present invention, since an uncross-linked polymer may not be strong enough for high-pressure chromatographic use. The cross-linking is also responsible for making the product polymer particles substantially insoluble in any solvents, including strong acidic or alkaline solution.

Apart from the use of functional monomers, additional monomers can be incorporated into a copolymerizable mixture in the present invention. The additional monomers may be hydrophobic and carry other functionality, preferably non-polar. Representative of such monomers are stryrene and the derivatives thereof.

As used herein, the term "macroporous polymers" refers to those having "macropores." In the present context, the "macropore" means pores of average diameter about 3.5 to about 10,000 nm. "Micropore" refers to pores of average diameter from about 0.10 to about 3.5 nm.

The polymer particles of the present invention can be prepared by the aqueous suspension polymerization of a copolymerizable mixture of a monomer, a cross-linker, and, if desired, a second monomer in the presence of a template polymer. In the suspension polymerization procedure, the various ingredients are thoroughly mixed prior to the start of the reaction. While this mixing of the ingredients can be done in a vessel apart from the reaction vessel, for convenience and practical reasons the mixing of the ingredients is normally conducted in the polymerization reaction vessel under an inert atmosphere, particularly where the monomers being employed are subjected to oxidation.

Polymerization proceeds at an elevated temperature, preferably above about 50° C. in the presence or absence of a catalyst. Suitable catalysts that can be used in the present invention include benzoyl peroxide, diacetylperoxide, and azo-bisisobutyronitrile. The amount of catalyst employed is within the range of about 0.005 to about 1.00% by weight, based on the weight of the monomer being polymerized. In the presence of a catalyst, the temperature of reaction is maintained above that at which the catalyst becomes active. Lower temperatures, e.g. about −70° to about 50° C., can be employed if high energy radiation is applied to initiate polymerization. The monomers and the template polymer are diluted in an aqueous medium at a level of from about 5 to about 50% by weight. Suitable aqueous medium comprises water and a water soluble polymer such as poly(vinyl alcohol).

Proper and sufficient agitation or stirring is required throughout the polymerization in order to produce the spherical and porous particles of polymer having the desired size. Thus, the polymerization mixture is agitated to disperse the monomers in the reaction medium by shear action, thereby forming droplets. These droplets should be of such size that when transformed into polymer particles, which are spherical, and porous, the same will be of the desired size. The polymer particles produced in accordance with the present invention preferably have a diameter in the range of about 3 to about 1000 microns. Various means are available to maintain the proper agitation. When polymerization is conducted in a reactor made of stainless steel, such reactor is preferably fitted with a rotatable shaft having one or more agitator blades. When a round-bottom flask is used as a reactor, an overhead stirrer will agitate the reaction medium. The amount of agitation necessary to obtain the desired results will vary depending upon the particular monomers being polymerized, as well as the particular polymer particle size desired. Therefore, the agitation speed such as the rpm (revolutions per minute) must be regulated within certain limits.

Polymerization times varies from about a few hours to a few days, depending on the reactivity of the monomers. After polymerization has proceeded to completion, the polymerization mixture is treated with a water-miscible solvent such as lower alcohol (methanol or ethanol) or acetone. The template polymer used can be removed from the product polymer by extraction with a suitable solvent. For example, if poly(acrylic acid) is the template polymer, it can be extracted into an aqueous alkaline solution. If poly(vinyl)pyridine is employed as the template polymer, aqueous acid solution may be used in the extraction. When the template polymer has formed a covalent bond with the functional monomer, the bond must be cleaved to recover the desired cross-linked polymer. If the covalent bond is an ester or amide linkage, it can be cleaved by alkaline hydrolysis or any other means known to one skilled in the art. Thus, the template polymer may be extracted into a suitable medium such as water, aqueous acid or alkaline solution, depending upon the reactivity of the particular template polymer. After the template polymer has been removed, the product polymer is washed with an appropriate solvent and dried. The dried material is in the form of separate round beads or agglomerates of beads. Agglomerates, if present, are divided into beads mechanically by dispersion in a non-solvent liquid, crushing or grinding.

While the cross-linked polymer phase in the polymer particle forms micropores, the voids which were once occupied by the template polymer molecules and which have resulted from extraction of the template polymer with the appropriate solvent form macropores. Thus, there are two distinctive types of pores of different sizes in the polymer matrix of the polymer particles of the present invention. In order to distinguish between both pore types, the spaces in which the micropores occupy in the polymer matrix are referred to as "microporous regions" and the spaces in which the macropores occupy in the polymer matrix are referred to as "macroporous regions."

Figure 1:
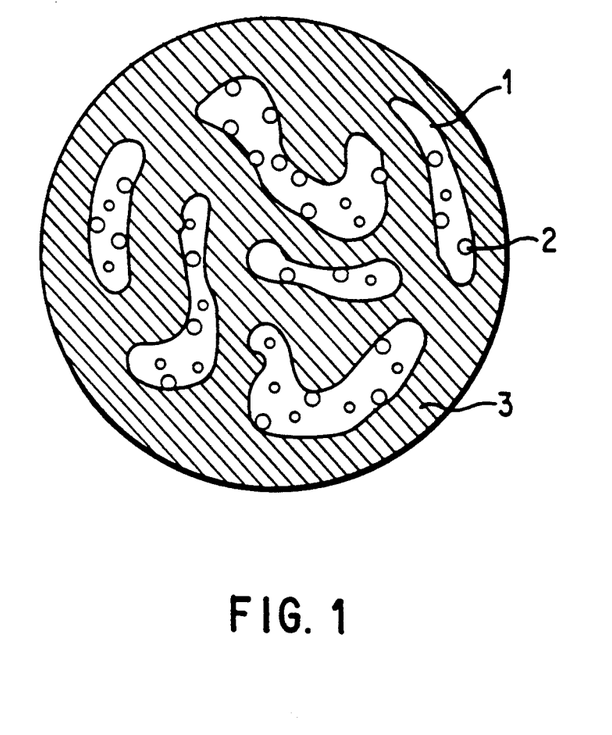
FIG. 1 is a graphic illustration of the polymer matrix of the polymer bead according to the present invention, where 1 represents a macroporous space, 2 represents a functional group, and 3 represents a cross-linked polymer phase.

After the template polymer molecules have been removed from the polymer matrix and the macroporous regions are formed, the functional groups originating from the functional monomer are populated on the surface of pores in the macroporous regions. By contrast, the microporous regions are substantially free from incorporation of the functional groups. The formation of the microporous and macroporous regions in the polymer matrix is illustrated in FIG. 1.

The functionality to be imparted to the cross-linked copolymer by the method of the present invention is generally polar in nature. A strong acidic group can be incorporated in the copolymer by selecting a monomer having a sulfonic acid group (e.g., 4-vinyl-p-toluenesulfonic acid) and a matching template polymer (e.g., poly(4-vinylpyridine). A weakly acidic group can be incorporated in the copolymer by selecting a monomer having a carboxylic acid and a matching template polymer. Alternatively, a carboxylic acid group can be generated by hydrolyzing a cross-linked acrylic-ester version (as shown in Scheme 2) of the templated polymer particles with a base such as an alkali metal hydroxide solution, to form carboxylic acid groups. Primary or secondary amino groups can be incorporated into the copolymer in a similar manner, providing a weakly basic functionality. If the amino group incorporated is tertiary, this group will be made into a strongly basic moiety by being quarternized with an alkyl halide.

The cross-linked porous polymer particles of the present invention will find an immediate use as an ion exchange resin or adsorbent in chromatography. However, their utility will not be limited to such use. Rather, the particle size, porosity, functionality, and surface area will determine the applications for the polymer beads of the present invention, and these characteristics can be predetermined by selection of the functional monomer, template polymer, and polymerization conditions (particularly agitation speed). Some of the potential uses not indicated herein are polymeric reagents and catalysts. Accordingly, the present invention provides a novel porous polymer particle having a wide variety of industrial uses and an equally novel process of making such polymer particles.

The present invention is illustrated by the following examples. However, it should be understood that the invention is not limited to the details of these examples.

EXAMPLE 1

In this example, the following reagents and solvents were used: Poly(acrylic acid) (PAA) (Aldrich, avg. MW 2,000; 250,000; 3,000,000 and 4,000,000); Divinylbenzene (DVB) (Dow Chem. Company, Midland, Mich.); 4-Vinyl pyridine 4-VPy) (Aldrich, Milwaukee, Wis., b.p. 62°–65° C./15 mm); α,α'-azobisisobutyronitrile (AIBN) (VASO ® 67 available from DuPont, Wilmington, Del.); Poly(vinyl alcohol) (PVA) (Aldrich, Milwaukee, Wis., MW 85,000–146,000, 98.99% hydrolyzed); acetone; methanol.

In the actual run, a Brinkman reactor or a round bottom flask equipped with an overhead stirrer was employed. A polymerizable mixture was prepared by admixing one part by mole PAA, one part by mole 4-VPy, one part by mole DVB and 0.5% by weight AIBN based on the total weight of the mixture. The mixture was filtered to remove any insoluble matter and flushed with nitrogen. First, five parts by volume of a 2% PVA aqueous solution was charged to the reactor. Then, one part by volume of the polymerizable mixture was charged to the reactor under stirring while the temperature in the reactor was maintained at 80° C. Reaction continued at 300-900 rpm for 12 hours. The polymerized material was washed with water, acetone and methanol to provide polymer beads. The beads were then extracted successively with acetone, 4N NaOH, and methanol in a Parr reactor under continuous shaking at room temperature for two days. The beads were dried to provide a 90% yield and tested for various physical properties. Under scanning electron microscope (SEM), the beads were determined to be spherical and to have a particle size of between 50 and 300 $\mu$m. The mechanical stability of the blades was assessed by packing them in a 150×4.6 mm HPLC column under high pressure. Minimal bead fracture was observed at a pressure up to 3,000 psi. After soaking the beads in 1N HCl and 4N HaOH for several days, there was neither swelling nor chemical degradation detectable by microscopic observation.

These and other results are summarized in Table 1.

TABLE 1

| Pore size: | >1 $\mu$m (SEM) |
|---|---|
| Pore size distribution: | Uniform (SEM) |
| Pore shape: | Normal (SEM) |
| Pore volume: | 1.9 ml/g |
| Apparent density: | 0.36 g/ml |
| Mechanical stability: | Excellent |
| Swelling resistance: | Excellent |
| Chemical stability: | Excellent |
| Cross-linking degree: | 10-50% |

Figure 2:
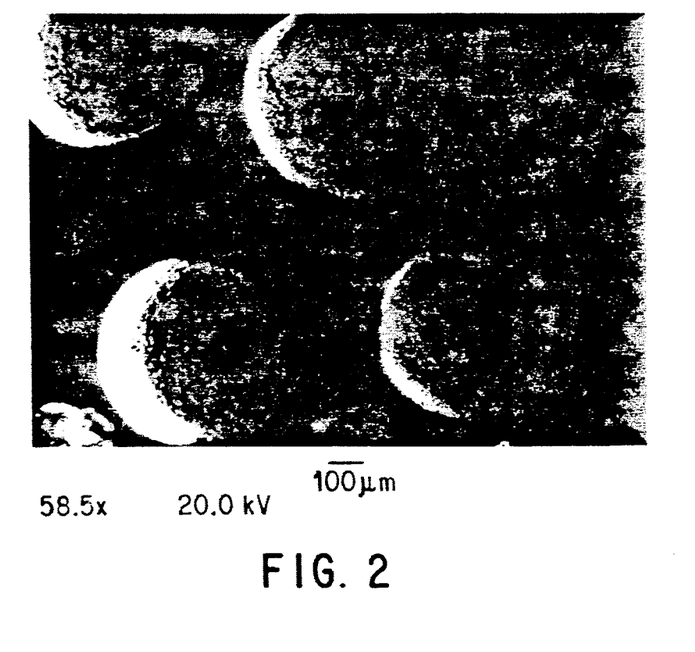
FIGS. 2–3 are photomicrographs of macroporous poly(vinyl pyridine/divinylbenzene) beads according to the present invention, with FIG. 1 being taken at ×58.5 and FIG. 2 being taken at ×115.
Figure 3:
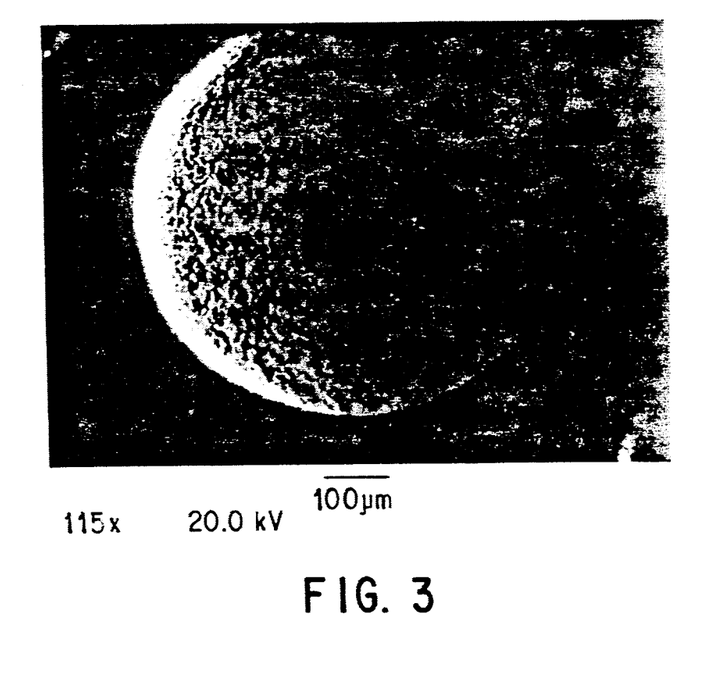
Figure 4:
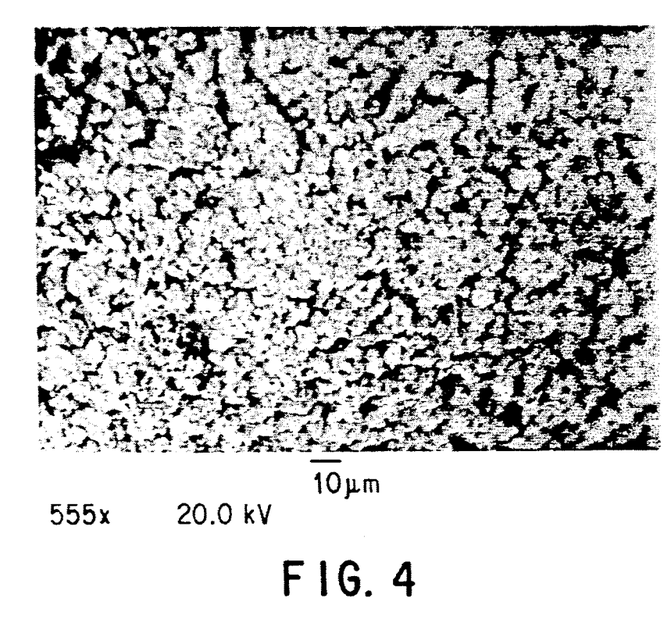
FIG. 4 is a photomicrograph of the polymer beads shown in FIGS. 2–3 at their surface (taken at ×555).
Figure 5:
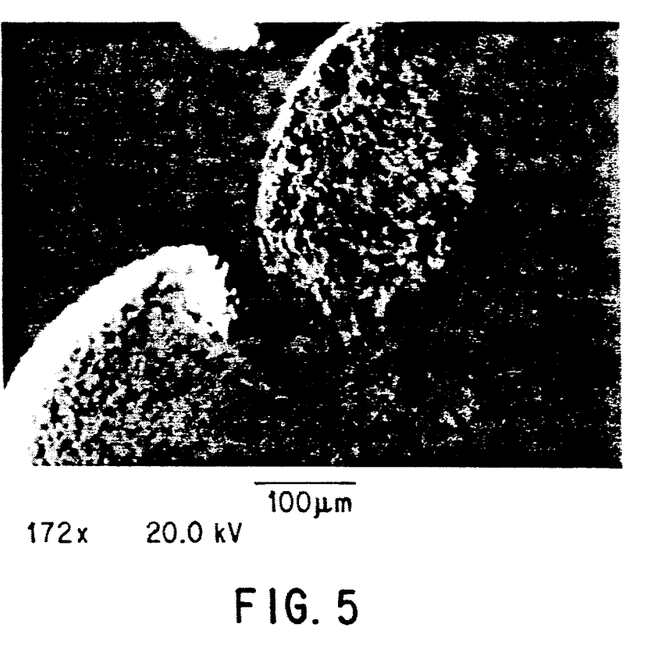
FIG. 5 is a photomicrograph of fragments or cross-section of the polymer beads shown in FIGS. 2–3 (taken at ×172).
Figure 6:
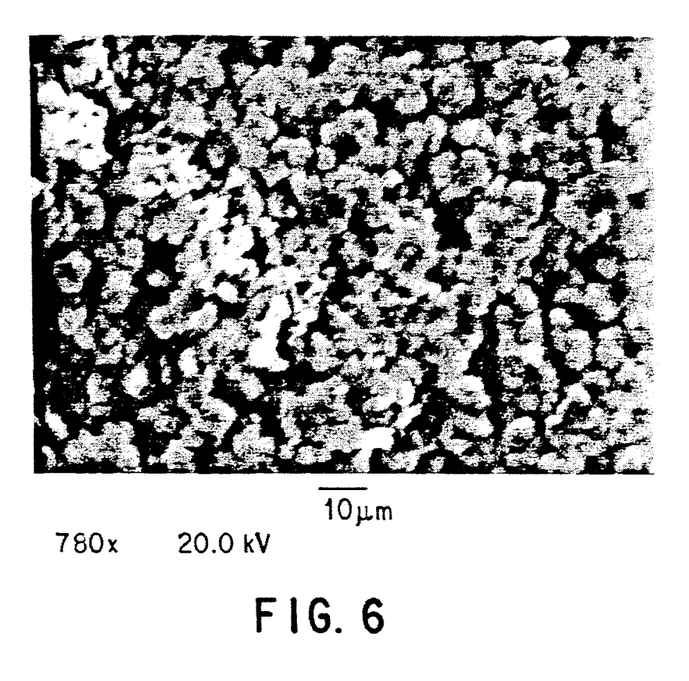
FIG. 6 is a photomicrograph of the bead fragments or cross-section shown in FIG. 5 at a higher magnification (taken at ×780).

A further scanning electron microscope (SEM) study was undertaken to reveal the pore morphology of the polymer beads of the present invention. FIGS. 2-3 clearly show the uniform spherical nature of the beads. FIG. 4 shows that the beads have large pores. The beads were broken to fragments and the fragments were examined for their cross-sectional surfaces under SEM. FIGS. 5-6 show the porous nature of the interior of the beads, where pores and interconnected channels are apparent.

Additionally, a confocal microscope study was undertaken to better understand how the functional groups incorporated are distributed within the polymer matrix of the beads. For a comparison purpose, polymer beads were prepared by polymerizing vinyl pyridine in the presence of polystyrene which does not interact with the monomer. Polystyrene was employed to provide the polymer with pores and channels, and did not fall within the definition of the template polymer as used in the present invention. The thus prepared beads as a control were compared with the beads of the present invention using the confocal microscopy. An objective of this study was to determine how pyridine groups differ from those incorporated in the control beads in the manner in which they are distributed in the beads. In order to locate pyridine groups within the polymer structure of beads, a negatively charged fluorescent dye—Evans Blue—was employed to illuminate pyridine under a confocal microscope. Thus, both the beads of the present invention and the control beads were treated with Evans Blue and examined under a confocal microscope.

A photomicrograph of the control beads shows that blue coloring is spread uniformly in the polymer matrix. This indicates that the pyridine groups are present in the macroporous region as well as in the microporous region with no selective localization in either region.

A photomicrograph of the beads of the present invention shows that blue coloring is confined to pores facing the macroporous region in the polymer. This indicates that the pyridine groups are located only in the macroporous region, not in the microporous region.

These various electron microscopy studies of the polymer beads of the present invention show the porous characteristics of the beads. Moreover, the photographs indicate that functional groups incorporated are essentially present in the macroporous region rather than being present in the microporous region.

The invention now being fully described, it will be apparent to one of ordinary skill in the art that many changes and modifications can be made without department from the spirit or scope of the invention.

We claim:

1. A method of preparing porous, functionalized polymer particles which comprises a cross-linked copolymer having microporous regions and macroporous regions in the polymer matrix thereof, wherein the functional groups are essentially present only within the macroporous regions, comprising the steps of:
   (a) providing a polymerizable mixture containing a functional monomer, a cross-linker and a template polymer in an aqueous medium to form a suspension, the template polymer being capable of forming an ionic or covalent bond with the functional monomer;
   (b) copolymerizing the monomer and the cross-linker with or without a polymerization catalyst in the suspension to form a cross-linked copolymer;
   (c) removing the aqueous medium and the template polymer from the copolymer to recover porous, functionalized polymer particles, the particles having microporous regions and macroporous regions in the polymer matrix thereof, wherein the functional groups are essentially present only within the macroporous regions.

2. The method according to claim 1, wherein the functional groups are polar.

3. The method according to claim 2, wherein the polar group is selected from the group consisting of hydroxyl, amino, carboxyl, sulfonyl, pyridiyl and phenol.

4. The method according to claim 1, wherein the functional monomer is a monoethylenically unsaturated monomer.

5. The method according to claim 4, wherein the unsaturated monomer is selected from the group consisting of vinylpyridine, vinylphenol, vinyl-p-toluenesulfonic acid, acrylic acid, methacrylic acid, and methacrylic acid halide.

6. The method according to claim 5, wherein the unsaturated monomer is vinylpyridine.

7. The method according to claim 1, wherein the template polymer is selected from the group consisting of poly(acrylic acid), poly(vinylalcohol), and poly(4-vinylpyridine).

8. The method according to claim 1, wherein the functional monomer is vinylpyridine and the template polymer is poly(acrylic acid).

9. The method according to claim 1, wherein the functional monomer is methacrylic acid halide and the template polymer is polyvinyl alcohol.

10. The method according to claim 1, wherein the functional monomer is vinyl-p-toluenesulfonic acid and the template polymer is poly(4-vinylpyridine).

11. The method according to claim 1, wherein in step (a) the template polymer forms an ionic bond with the functional monomer.

12. The method according to claim 10, wherein in step (c) the removal of the template polymer involves extraction with an aqueous alkali or acid solution.

13. The method according to claim 1, wherein in step (a) the template polymer forms a covalent bond with the functional monomer.

14. The method according to claim 13, wherein the covalent bond is an ester or amido.

15. The method according to claim 13, wherein in step (c) the removal of the template polymer involves hydrolysis of the copolymer.

16. The method according to claim 1, wherein the copolymerization is conducted at a temperature of above about 50° C.

17. The method according to claim 16, wherein the catalyst is AIBN.

18. The method according to claim 1, wherein the cross-linked copolymer has a crosslinking degree of about 10 to about 50%.

* * * * *